United States Patent [19]

Robins et al.

[11] Patent Number: 5,041,542

[45] Date of Patent: Aug. 20, 1991

[54] SUBSTITUTED PYRIMIDO[5,4-D]PYRIMIDINE NUCLEOSIDES

[75] Inventors: Roland K. Robins; Ganapathi R. Revankar; Yogesh S. Sanghvi, all of Irvine, Calif.

[73] Assignee: Nucleic Acid Research Institute, Costa Mesa, Calif.

[21] Appl. No.: 202,787

[22] Filed: Jun. 3, 1988

[51] Int. Cl.$^5$ ............................................. C07H 19/23
[52] U.S. Cl. ....................................... 536/24; 536/26; 536/22
[58] Field of Search ....................... 536/22, 23, 24, 26; 514/45, 46

[56] References Cited

U.S. PATENT DOCUMENTS 4,801,698  1/1989  Cook et al. ........................... 536/28

OTHER PUBLICATIONS

Goodman, "Chemical Synthesis and Transformations of Nucleosides" in Basic Principles in Nucleic Acid Chemistry, Ts'O ed., vol. 1, Academic Press, New York, 1974, pp. 152–161.
Cusack et al., J. Chem. Soc. Perkin I, 1973, pp. 1720–1731.
Westover et al., J. Med. Chem., 24, 941–946 (1981).
Berman et al., Tett. Lett., 1973 (33), pp. 3099–3101.

*Primary Examiner*—Johnnie R. Brown
*Assistant Examiner*—L. Eric Crane
*Attorney, Agent, or Firm*—Herb Boswell

[57] ABSTRACT

α and β-ribonucleosides of substituted pyrimido[5,4-d]pyrimidines are used in treating malignant tumors in vivo. A novel synthesis for preparing these compounds and other related compounds is further disclosed.

3 Claims, No Drawings

SUBSTITUTED PYRIMIDO[5,4-D]PYRIMIDINE NUCLEOSIDES

BACKGROUND OF INVENTION

This invention is directed to α and β-ribonucleosides of substituted pyrimido[5,4-d]pyrimidines and to the use of these compounds in treating malignant tumors in vivo. A novel synthesis for preparing these compounds and other related compounds is further disclosed.

While the arsenal of chemotherapeutic agents for treating neoplastic diseases includes a number of clinically useful agents, control of malignant tumors in warm blooded animals still remains a much sought after goal.

Recent molecular biology and biochemistry studies of purine and purine nucleoside analogs showing potent antiviral and antitumor activity have uncovered a number of new potential targets. The pyrimido[5,4-d]pyrimidine ring system has attracted considerable attention in recent years as the deaza-analog of the naturally occurring antibiotics toxoflavin and fervenulin. Dipyridamole, a pyrimido[5,4-d]pyrimidine derivative, has shown coronary vasodilator properties. The synthesis of the naturally occurring exocyclic aminonucleoside clitocine has also been reported.

The synthesis and the biological properties of an unusual exocyclic aminonucleoside, 4-amino-8-(β-D-ribofuranosylamino)pyrimido[5,4-d]pyrimidine (hereinafter alternately referred to as ARPP) has also been reported, see Westover et al. *J. Med. Chem.* (1981), 24, 941–946. ARPP has shown antiviral activity for DNA and RNA viruses in cell culture by inhibiting viral protein synthesis. ARPP exhibits immunosuppressive activity and inhibits the growth of L1210 leukemia in mice.

Molecular mechanics calculation of ARPP and certain related nucleosides has shown that their conformational behavior is very similar even when groups like chloro or amino are introduced at positions 2 and/or 6. Other studies on the modification of the glycon moiety of ARPP resulted in the loss of antiviral and antitumor activity, see Srivastava et al. *J. Med. Chem.* (1981), 24, 393–398.

In view of the inability of current cancer chemotherapeutics to successfully control all neoplastic diseases, it is evident that there exists a need for new and additional cancer chemotherapeutic agents.

Further, there exists a need for new and better preparative procedures for the synthesis of pyrimido[5,4-d]pyrimidines nucleosides.

BRIEF DESCRIPTION OF THE INVENTION

The present invention includes a novel class of α and β-ribonucleosides of substituted pyrimido[5,4-d]pyrimidines of the formula:

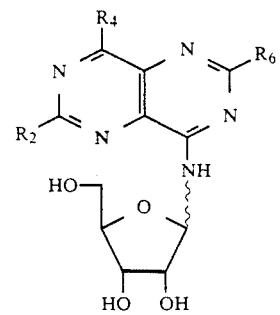

wherein $R_2$, $R_4$ and $R_6$ are independently selected from H, OH, $NH_2$, $OCH_2Ph$, Cl, Br, $OCH_3$, NHMe and $NMe_2$ with the proviso that when $R_4$ is $NH_2$: $R_2$ and $R_6$ are not H.

Further in accordance with the invention α and β-ribonucleosides of substituted pyrimido[5,4-d]pyrimidines are useful in treating malignant tumors in warm blooded animals.

Additionally according to this invention the antitumor properties of certain α and β-ribonucleosides of pyrimido[5,4-d]pyrimidines are achieved by administering to a warm blooded animal an effective amount of a pharmaceutical composition containing α and β-ribonucleosides of substituted pyrimido[5,4-d]pyrimidines or pharmaceutically acceptable salts thereof as the active compound in at least 0.1% by weight based on the total weight of the composition.

Particularly useful as antitumor agents are the α and β anomers of 4-methoxy-8-(D-ribofuranosylamino)-pyrimido[5,4-d]pyrimidine.

Compounds of the invention are particular advantageous for treating tumors including but not necessary limited to carcinomas, sarcomas and leukemias—particularly solid slow growing tumors. The method of treating is effective in bringing about regression, palliation, inhibition of growth and remission of tumors.

For use in pharmaceutical compositions of the invention a pharmaceutical carrier would be utilized. Preferredly the carrier would be chosen to allow for administration of a suitable concentration of the α and β-ribonucleosides of substituted pyrimido[5,4-d]pyrimidines either by oral administration, ophthalmic administration, topical administration, suppository administration or by suitable injection as a solution or suspension into the affected warm blooded animal. The dose and choice of administration of α and β-ribonucleosides of substituted pyrimido[5,4-d]pyrimidines of the invention would be dependent upon the host harboring the tumor disease state, the type of tumor and the tumor site. For injection, α and β-ribonucleosides of substituted pyrimido[5,4-d]pyrimidines of the invention could be administered intravenously, intramuscularly, intracerebrally, subcutaneously or intraperitoneally. Further, for facilitating the use of α and β-ribonucleosides of substituted pyrimido[5,4-d]pyrimidines, a physiologically accepted salt could be used. Presently it is preferred to administer the compound by injection.

Further, the invention includes a novel process for the preparation of α and β-ribonucleosides of substituted pyrimido[5,4-d]pyrimidines and related compounds. In this novel process α and β-ribonucleosides of substituted pyrimido[5,4-d]pyrimidines are prepared from treatment of 2,4,6,8-tetrachloropyrimido[5,4-d]pyrimidine with 2,3-O-isopropylidene-D- ribofuranosylamine followed by nucleophilic displacement, hydrogenation and deisopropylidenation to give compounds of the formula:

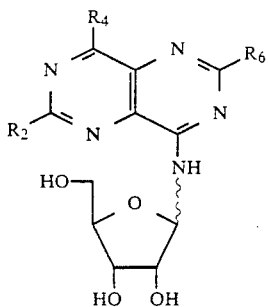

wherein $R_2$, $R_4$ and $R_6$ are independently selected from H, OH, $NH_2$, $OCH_2Ph$, Cl, Br, $OCH_3$, NHMe, $NMe_2$.

This novel process can also be utilized to prepare other related compounds such as the $SCH_3$ analogs of the above mentioned $OCH_3$ and other thio analogs.

DETAILED DESCRIPTION OF INVENTION

In the novel process of the invention the direct condensation of a halogen substituted pyrimido[5,4-d]pyrimidine with an aminoglycoside results in a one step synthesis of the desired exocyclic aminonucleoside. Thus, treatment of free 2,3-O-isopropylidene-D-ribofuranosylamine [see Cusack et al., *J. Chem. Soc., Perkin Trans.* 1 (1973), 1720-1731], (generated in situ from its stable tosylate salt 2 by the addition of $Et_3N$) with dry 2,4,6,8-tetrachloropyrimido[5,4-d]pyrimidine (1) [see Fisher et al., *Leibig. Ann. Chem.* (1960), 631, 147-162] in 1-butanol at room temperature gave a mixture of two nucleoside products which were separated by silica gel column chromatography and identified as 2,4,6-trichloro-8-(2,3-O-isopropylidene-β-D-ribofuranosylamino)pyrimido[5,4-d]pyrimidine (3) and its α-anomer (4) (see Scheme I).

The anomeric ratio of 3:4 was 1.0:0.77. The assignment of the anomeric configuration of 3 and 4 was inconclusive from the $^1$H NMR coupling constant values of the anomeric protons, since there was no significant difference in J values (10.8 Hz and 10.0 Hz for 3 and 4, respectively). Thus, $^1$H-$^1$H 2D NMR of these two compounds were studied. The less polar compound 3 revealed an anomeric proton centered at δ6.34 ppm (d, J=10.8 Hz) coupled to another proton at δ9.09 ppm (d, J=10.8 Hz). Upon $D_2O$ addition, the anomeric proton collapsed to a singlet and the downfield proton exchanged, indicating that the sugar moiety is located at the exocyclic amino group.

The appearance of the NH proton at low field is expected due to hydrogen bonding between the 5'OH and NH groups. This suggested a β-configuration for compound 3. Imbach's imperical rule, formulated for determining the anomeric configuration of azole nucleosides using the difference between the chemical shifts of the protons of the methyl groups of the dioxolane rings did not prove helpful since the compound 3 exhibited Δδ0.22 ppm for the methyl groups, while compound 4 showed Δδ0.25 ppm. Furthermore, compound 4 revealed an anomeric proton at δ6.19 ppm and an NH proton at δ8.23 ppm. This high field placement of NH proton for 4 is due to the lack of hydrogen bonding between the 5'OH and NH groups, because of the α-configuration. Moreover, these compounds mutarotate in solution, especially in $Me_2SO-d_6$. Mutarotation of similar aminoglycosides has been documented. The anomeric configuration of 3 was established as β by X-ray diffraction analysis. The anomeric configuration of 4 was then assigned as α.

2,6-Dichloro-4-n-butyloxy-8-(2,3-O-isopropylidene-β-D-ribofuranosylamino)pyrimido[5,4-d]pyrimidine (5) was isolated as a product of the solvent (1-butanol) participation when the reaction mixture of 1 and 2 was left for 16 h at ambient temperature, indicating the susceptibility of the 4-chloro group of 3 towards nucleophilic displacement reactions. Although the formation of the α-anomer of 5 was detected by TLC in the reaction mixture, it was not isolated.

A brief (30 min at 0° C.) treatment of 3 and 4 with $EtOH/NH_3$ (saturated at 0° C.) resulted in the formation of 4-amino-2,6-dichloro-8-(2,3-O-isopropylidene-β-D-ribofuranosyl-amino)pyrimido[5,4-d]pyrimidine (6) and its α-anomer (9), respectively. Single-crystal X-ray study of 9 established the α-configuration, and hence to its precursor 4. Catalytic (Pd/C) hydrogeneration of 6 and 9 at 50 psi for 24 h gave 4-amino-8-(2,3-O-isopropylidene-β-D-ribofuranosylamino)pyrimido[5,4-d]pyrimidine (7) and the α-anomer 10, respectively (Scheme II).

Careful treatment of 7 and 10 with aqueous trifluoroacetic acid (90% TFA) at room temperature cleaved the isopropylidene group to give ARPP (8) and its α-anomer 11 in >80% yield, respectively. The physical properties (mp, TLC, HPLC, UV and $^1$H NMR) of 8 were identical with those of a standard sample of ARPP, the structure of which had been confirmed previously by X-ray studies. The anomeric protons of 8 and 11 appear at δ5.88 ppm and δ6.15 ppm, respectively. This observation is in agreement with the assignment of the anomeric protons for the α-anomer at lower field when compared to the β-anomer as in the case of similar exocyclic aminonucleosides recently reported.

A nucleophilic displacement of the 4-chloro group from 3 and 4 with NaOMe in MeOH furnished 2,6-dichloro-4-methoxy-8-(2,3-O-isopropylidene-β-D-ribofuranosylamino)pyrimido[5,4-d]pyrimidine (12) and the α-anomer 15, respectively. Catalytic hydrogenation of 12 and 15 yielded 13 and 16, which on independent deisopropylidenation gave 4-methoxy-8-(β-D-ribofuranosylamino)pyrimido[5,4-d]pyrimidine (MRPP, 14) and the α-anomer 17, respectively. 14 Is assigned as the β-anomer and 17 as the α-anomer on the basis of their $^1$H NMR data. The anomeric proton of 14 exhibited a quartet at δ5.83 ppm, which on comparison with the anomeric proton of 17 was 0.33 ppm upfield (δ6.16 pm). The exocyclic NH proton of 14 revealed a doublet at δ8.71 ppm, and the NH proton of 17 appeared at δ8.39 ppm. This observation is consistent with the higher field NH proton of 11 (δ8.19 ppm) and the lower field NH proton of 8 (δ8.34 ppm).

A mild method for the preparation of 21 was utilized in order to obtain the inosine analog of ARPP. When 3 was stirred with benzyl alcohol in the presence of $Et_3N$ at room temperature for 24 h, 4-benzyloxy-2,6-dichloro-8-(2,3-O-isopropylidene-β-D-ribofuranosylamino)-pyrimido[5,4-d]pyrimidine (18) was obtained in >60% yield. Debenzylation of 18 by hydrogenation in the presence of Pd/C at atmospheric pressure in dioxane gave 2,6-dichloro-8-(2,3-O-isopropylidene-β-D-ribofuranosylamino)pyrimido[5,4-d]pyrimidin-4(3H)-one (19). Deisopropylidenation of 19 with aqueous TFA furnished 2,6-dichloro-8-(β-D- ribofuranosylamino)pyrimido[5,4-d]pyrimidin-4(3H)-one, which on dehalogenation furnished 8-(β-D-ribofuranosylamino)pyrimido[5,4-d]pyrimidin-4(3H)-one (21) in 66% yield. However, hydrogenation of 18 in MeOH in the presence of Pd/C resulted in solvent participation to furnish 13 and not 8-(2,3-O-isopropylidene-β-D-ribofuranosylamino)pyrimido[5,4-d]pyrimidin-4(3H)-one (20).

A nucleophilic displacement of the 4-chloro group of 3 with $NH_2Me$ and $NHMe_2$ gave the corresponding 2,6-dichloro-4-methylamino-(22) and 4-dimethylamino-8-(2,3-O-isopropylidene-β-D-ribofuranosylamino)-pyrimido[5,4-d]pyrimidine (25). Hydrogenation of 22 and 25 provided 23 and 26, respectively. Subsequent deisopropylidenation of 23 and 26 gave 4-methylamino-8-(β-D-ribofuranosylamino)pyrimido[5,4-d]pyrimidine (24) and 4-dimethylamino-8-(β-D-ribofuranosylamino)-pyrimido[5,4-d]pyrimidine (27), respectively.

Controlled hydrogenation of 6 removed the 2-chloro group to furnish 4-amino-6-chloro-8-(2,3-O-isopropylidene-β-D-ribofuranosylamino)pyrimido[5,4-d]pyrimidine (36) in 65% yield. The proton NMR of 36 exhibited a singlet at $\delta 8.35$ ppm for $C_2H$, thus confirming the removal of only one chloro group from 6. The structure of this selective dehalogenation product was established by a single-crystal X-ray diffraction analysis to be 36. Subsequent deisopropylidenation of 36 gave 4-amino-6-chloro-8-(β-D-ribofuranosylamino)pyrimido[5,4-d]pyrimidine (37) in 67% yield (Scheme III).

Thus, treatment of 6 with liquid $NH_3$ over a period of 6 days furnished a mixture of two nucleoside products. After separation by flash chromatography, the structure of the major product (59% yield) was assigned as the β-anomer 33 and the minor product (15% yield) as the α-anomer of 33. Catalytic hydrogenation of 33 furnished 34 whose $^1H$ NMR spectrum exhibited a $C_2H$ proton at $\delta 8.05$ ppm. In an effort to confirm the site of the ammonolysis in 6 an unambiguous synthesis of 34 from 4,6,8-trichloropyrimido[5,4-d]pyrimidine (28) was effected. Treatment of 28 with 2 as described earlier for the preparation of 3, furnished an air sensitive mixture of two compounds, presumably an anomeric mixture of 4,6-dichloro-8-(2,3-O-isopropylidene-D-ribofuranosylamino)pyrimido[5,4-d]pyrimidine (29). A brief $EtOH/NH_3$ treatment of 29 gave a mixture of two products, from which compound 36 was isolated as a major product. This compound was found to be identical to 36 prepared previously from 6, thus confirming the structural assignment.

Compound 29 upon ammonolysis (6 days) furnished an alternate route for the synthesis of 34. This established the preferential site of the nucleophilic substitution at position 6 over position 2 in the compound 6. While we do not wish to be bound by theory, on the basis of the reactivity of various chloro groups in 1 and 28, we suggest an order of nucleophilic substitution as positions 8>4>6>2.

Deisopropylidenation of 34 gave the desired 4,6-diamino-8-(β-D-ribofuranosylamino)pyrimido[5,4-d]pyrimidine (35), isolated as a TFA salt (Scheme III). Treatment of 29 with benzyl alcohol in a similar manner as described earlier for the preparation of 18 furnished 30. Hydrogenation of 30 gave 31, which on aqueous TFA treatment provided 6-chloro-8-(β-D-ribofuranosylamino)pyrimido[5,4-d]pyrimidin-4(3H)-one (32) in 58% yield.

Melting points (uncorrected) were determined in a Thomas-Hoover capillary melting point apparatus. Elemental analyses were performed by Robertson Laboratory, Florham Park, N.J. Thin-layer chromatography (TLC) was conducted on plates of silica gel 60 F-254 (EM Reagents). Silica gel (E. Merck: 230–400 mesh) was used for flash column chromatography. All solvents used were reagent grade. Detection of nucleoside components in TLC was by UV light, and with 10% $H_2SO_4$ in MeOH spray followed by heating. Evaporations were conducted under diminished pressure with the bath temperature below 30° C. Infrared (IR) spectra were recorded with a Beckman Acculab 2 spectrophotometer and ultraviolet (UV) spectra were recorded on a Beckman DU-50 spectrophotometer. Nuclear magnetic resonance ($^1H$ NMR) spectra were recorded at 300 MHz with an IBM NR/300 spectrometer. The chemical shift values are expressed in δ values (parts per million) relative to tetramethylsilane as an internal standard. The signals are described as s (singlet), d (doublet), t (triplet), q (quartet), and m (multiplet). The presence of solvent as indicated by elemental analysis was verified by $^1H$ NMR spectroscopy.

EXAMPLE 1

2,4,6-Trichloro-8-(2,3-O-isopropylidene-β-and α-D-ribofuranosylamino)pyrimido[5,4-d]pyrimidine (3 and 4)

A suspension of dry 2,3-O-isopropylideneribofuranosylamine p-toluenesulfonate (2, 3.61 g, 10 mmol) in 1-butanol (200 mL) was treated with $Et_3N$ (4.18 mL, 30 mmol) and the mixture was stirred at ambient temperature under anhydrous conditions furnishing a clear solution in 30 min. Finely powdered, dry 2,4,6,8-tetrachloropyrimido[5,4-d]pyrimidine (1, 4.04 g, 15 mmol) was added to the above solution and stirred for 6 h under similar conditions. The solution was evaporated and the residue dissolved in EtOAc (300 mL), filtered to remove some insoluble material and washed with water (2×100 mL). After drying ($Na_2SO_4$), the solvent was evaporated and the residue was purified on a flash silica gel column (5×45 cm) by using hexanes/EtOAc (7:3, v/v), as the eluent which provided two products in the following order:

(i) 2,4,6-Trichloro-8-(2,3-O-isopropylidene-β-D-ribofuranosylamino)pyrimido[5,4-d]pyrimidine (3: 1.89 g, 45%): Rf 0.65 (EtOAc:hexanes 3:7): mp 1630° C. (EtOH): IR (KBr) $v_{max}$ 845 (C-Cl), 3300, 3455 (OH, NH) $cm^{-1}$: UV (MeOH) $\lambda_{max}$ nm ($\epsilon \times 10^{-3}$) 256 (6.7), 298 (7.9), 346 (9.2) and 362 (sh) (7.3): $^1H$ NMR ($CDCl_3$) δ1.37 and 1.59 (2 s, 6, $2CH_3$), 2.61 (br s, 1, $C_5'OH$), 3.94 (s, 2, $C_5'CH_2$), 4.48 (s, 1, $C_4'CH$), 4.78 and 5.02 (2 m, 2, $C_2',_3'H$), 6.34 (d, 1, J=10.8 Hz, $C_1'H$), and 9.09 (br d, 1, J=10.8 Hz, NH). Anal. ($C_{14}H_{14}Cl_3N_5O_4$) C, H, N, Cl.

(ii) 2,4,6-Trichloro-8-(2,3-O-isopropylidene-α-D-ribofuranosylamino)pyrimido[5,4-d]pyrimidine (4: 1.47 g, 35%): Rf 0.55 (EtOAc:hexanes, 3:7): mp 99° C. $^1H$ NMR ($CDCl_3$) δ1.42 and 1.71 (2 s, 6, $2CH_3$), 2.50 (br s, 1, $C_5'OH$), 3.77–3.91 (m, 2, $C_5'CH_2$), 4.27 (m, 1, $C_4'H$), 4.92 (m, 2, $C_2'_3'H$), 6.19 (m, 1, $C_1'H$), and 8.23 (br d, 1, J=10.0 Hz, NH). Anal. ($C_{14}H_{14}Cl_3N_5O_4.0.5EtOH$) C, H, N, Cl.

EXAMPLE 2

2,6-Dichloro-4-n-butyloxy-8-(2,3-O-isopropylidene-β-D-ribofuranosylamino)pyrimido[5,4-d]pyrimidine (5)

The title compound was obtained in 30% yield when the above reaction mixture was left for 16 h or longer at ambient temperature and when a reverse addition of free glycosylamine 2 was made to a solution of 1 in 1-butanol. Rf 0.68 (EtOAc:hexanes, 3:7): mp 175° C.: $^1$H NMR (CDCl$_3$) δ1.00 (t, 3, CH$_2$CH$_3$), 1.39 and 1.61 (2 s, 6, 2CH$_3$), 1.52 (m, 2, CH$_2$CH$_3$), 1.92 (m, 2, CH$_2$CH$_2$), 2.79 (br s, 1, C$_5$'OH), 3.94 (m, 2, C$_5$'CH$_2$), 4.46 (br s, 1, C$_4$'H), 4.63 (m, 2, OCH$_2$), 4.84 and 5.02 (2 m, 2, C$_2$'$_3$'H), 6.27 (d, 1, J=10.5 Hz, C$_1$'H), 8.69 (d, 1, J=10.5 Hz, NH). Anal. (C$_{18}$H$_{23}$Cl$_2$N$_5$O$_5$.0.25H$_2$O) C, H, N, Cl.

EXAMPLE 3

2,6-Dichloro-4-amino-8-(2,3-O-isopropylidene-β-D-ribofuranosylamino)pyrimido[5,4-d]pyrimidine (6)

A solution of 3 (0.85 g, 2 mmol) in EtOH/NH$_3$ (20 mL, saturated at 0° C.) was stirred at 0° C. for 30 min. The solvent was removed, and the residue was purified by chromatography on a silica gel column (5×45 cm) using hexanes/EtOAc (1:3, v/v) as the eluent to provide 0.59 g (74%) of 6: mp 148° C. (EtOH/hexanes): $^1$H NMR (CDCl$_3$) δ1.37 and 1.59 (2 s, 6, 2CH$_3$), 2.86 (t, 1, C$_5$'OH), 3.85–3.98 (m, 2, C$_5$'CH$_2$), 4.44 (br s, 1, C$_4$'H), 4.83 and 5.00 (m, 2, C$_2$'$_3$'H), 6.15 and 6.79 (2 br s, 2, NH$_2$), 6.22 (d of d, 1, C$_1$'H) and 8.47 (d, 1, J=10.5 Hz, NH). Anal. (C$_{14}$H$_{16}$Cl$_2$N$_6$O$_4$), C, H, N, Cl.

EXAMPLE 4

2,6-Dichloro-4-amino-8-(2,3-O-isopropylidene-α-D-ribofuranosylamino)pyrimido[5,4-d]pyrimidine (9)

The title compound was prepared in a similar manner as described for 6, by using 4 (0.85 g, 2 mmol) and EtOH/NH$_3$ (20 mL). The product was isolated as a crystalline solid and recrystallized from EtOH to yield 0.56 g (70%): mp 208° C.: $^1$H NMR (CDCl$_3$) δ1.47 and 1.74 (2 s, 6, 2CH$_3$), 2.78 (t, 1, C$_5$'OH), 3.76–3.92 (2 m, 2, C$_5$'CH$_2$), 4.27 (t, 1, C$_4$'H), 4.92 (m, 2, C$_2$'$_3$'H), 6.18 (m, 1, C$_1$'H), 6.54 and 6.69 (2 br s, 2, NH$_2$) and 8.00 (d, 1, J=10.5 Hz, NH). Anal. (C$_{14}$H$_{16}$Cl$_2$N$_6$O$_4$.0.25EtOH), C, H, N, Cl.

EXAMPLE 5

General procedure for hydrogenation

A mixture of the appropriate nucleoside (1 mmol), Pd/C (10%: 0.1 g), and anhydrous Et$_3$N (3 mmol) in absolute EtOH (100 mL) was shaken in a pressure bottle on a Parr hydrogenator at 50 psi for 24 h at ambient temperature. The catalyst was removed by filtration through a Celite pad and washed with EtOH (2×25 mL). The combined filtrates were evaporated and the residue was purified by either column chromatography or direct crystallization.

EXAMPLE 6

4-Amino-8-(2,3-O-isopropylidene-β-D-ribofuranosylamino)pyrimido[5,4-d]pyrimidine (7)

Hydrogenation of 6 by the general procedure gave 7 in 75% yield: mp 178° C. (EtOH): $^1$H NMR (Me$_2$SO-d$_6$) δ1.28 and 1.47 (2 s, 6, 2CH$_3$), 3.51 (m, 2, C$_5$'CH$_2$), 4.18 (m, 1, C$_4$'H), 4.81 (m, 2, C$_2$'$_3$'H), 5.54 (t, 1, C$_5$'OH), 6.10 (d, 1, J=9.4 Hz, C$_1$'H), 7.80 and 7.99 (2 br s, 2, NH$_2$), 8.36 and 8.49 (2 s, 2, C$_2$H and C$_6$H), and 8.83 (d, 1, J=10.6 Hz, NH). Anal. (C$_{14}$H$_{18}$N$_6$O$_4$) C, H, N.

EXAMPLE 7

4-Amino-8-(2,3-O-isopropylidene-α-D-ribofuranosylamino)pyrimido[5,4-d]pyrimidine (10)

Hydrogenation of 9 by the general procedure gave 10 in 71% yield: isolated as homogeneous foam: $^1$H NMR (Me$_2$SO-d$_6$) δ1.36 and 1.55 (2 s, 6, 2CH$_3$), 3.52 (m, 2, C$_5$'CH$_2$), 4.00 (m, 1, C$_4$'H), 4.83 (m, 2, C$_2$'$_3$'H), 5.07 (t, 1, C$_5$'OH), 6.15 (d of d, 1, C$_1$'H), 7.68 (d, 1, J=10.4 Hz, NH), 7.89 and 8.08 (2 br s, 2, NH$_2$), 8.40 and 8.55 (2 s, 2, C$_2$H and C$_6$H). Anal. (C$_{14}$H$_{18}$N$_6$O$_4$) C, H, N.

EXAMPLE 8

General procedure for deisopropylidenation reaction

A suspension of the corresponding 2',3'-O-isopropylidenenucleoside (0.5 mmol) in a mixture of TFA/H$_2$O (2 mL: 9:1, v/v) was stirred at room temperature for 30 min. The solvent was evaporated under a stream of argon and the residue was coevaporated with EtOH (3×20 mL), redissolved in EtOH (2 mL) and precipitated by slow addition of dry diethyl ether (100 mL). Compounds were further purified by flash silica gel column chromatography using EtOAc/H$_2$O/MeOH/acetone (3:1:1:1, v/v) as the eluent or by HPLC followed by crystallization from a suitable solvent.

EXAMPLE 9

4-Amino-8-(β-D-ribofuranosylamino)pyrimido[5,4-d]pyrimidine (ARPP, 8)

Deisopropylidenation of 7 with aqueous TFA gave 8 in 85% yield: mp 212° C. (H$_2$O) [lit mp 214°–216° C.]: UV and $^1$H NMR spectra are identical with an authentic sample of 8.

EXAMPLE 10

4-Amino-8-(α-D-ribofuranosylamino)pyrimido[5,4-d]pyrimidine (11)

Deisopropylidenation of 10 with aqueous TFA gave 11 in 82% yield: mp 165° C. (EtOH): $^1$H NMR (Me$_2$SO-d$_6$) δ3.50 (m, 2, C$_5$'CH$_2$), 3.77, 3.96 and 4.11 (3 m, 3, C$_2$'$_3$'$_4$'H), 4.91 (t, 1, C$_5$'OH), 5.31 and 5.64 (2 d, 2, J=5.6 Hz, C$_2$'$_3$'OH), 5.78 and 5.97 (2 q, 1, C$_1$'H, collapsed to d, J=5.6 Hz after deuteration), 7.78 and 8.0 (2 br s, 2, NH$_2$), 8.19 (d, 1, J=10.5 Hz, NH), 8.38 and 8.49 (2 s, 2, C$_2$H and C$_6$H). Anal. (C$_{11}$H$_{14}$N$_6$O$_4$) C, H, N.

EXAMPLE 11

2,6-Dichloro-4-methoxy-8-(2,3-O-isopropylidene-β-D-ribofuranosylamino)pyrimido[5,4-d]pyrimidine (12)

To a stirred solution of 3 (0.42 g, 1 mmol) in dry MeOH (20 mL) was added NaOMe (0.108 g, 2 mmol). When TLC (solvent - EtOAc:hexanes, 3:7) showed the reaction is complete (in 30 min), the solution was neutralized by the addition of dowex-50 (H+) resin and filtered. The resin was washed with MeOH (2×20 mL) and the combined filtrates were evaporated to dryness. The residue was purified by flash chromatography using hexanes/EtOAc (3:1 v/v) as the eluent to furnish 0.27 g (65%) of 12: mp 211° C. (EtOH): $^1$H NMR (CDCl$_3$) δ1.26 and 1.48 (2 s, 6, 2CH$_3$), 2.49 (br s, 1, C$_5$'OH), 3.62 (m, 2, C$_5$'CH$_2$), 4.11 (s, 3, OCH$_3$), 4.34 (s, 1, C$_4$'H), 4.69 and 4.89 (2 m, 2, C$_2$'$_3$'H), 6.15 (d of d, 1, C$_1$'H), and 8.57 (d, 1, J=10.8 Hz, NH). Anal. (C$_{15}$H$_{17}$Cl$_2$N$_5$O$_5$) C, H, N, Cl.

EXAMPLE 12

4-Methoxy-8-(2,3-O-isopropylidene-β-D-ribofuranosylamino)pyrimido[5,4-d]pyrimidine (13)

The title compound was prepared by hydrogenation of 12 following the general procedure, in 84% yield: mp 218° C. (EtOH): $^1$H NMR (Me$_2$SO-d$_6$) δ1.28 and 1.47 (2 s, 6, 2CH$_3$), 3.55 (m, 2, C$_5'$CH$_2$), 4.11 (s, 3, OCH$_3$), 4.20 (s, 1, C$_4'$H), 4.82 (m, 2, C$_2'_3'$H), 5.63 (br s, 1, C$_5'$OH), 6.13 (br s, 1, C$_1'$H), 8.60 and 8.79 (2 s, 2, C$_2$H and C$_6$H), and 9.11 (br s, 1, NH). Anal. (C$_{15}$H$_{19}$N$_5$O$_5$) C, H, N.

EXAMPLE 13

4-Methoxy-8-(β-D-ribofuranosylamino)pyrimido[5,4-d]pyrimidine (14)

Deisopropylidenation of 13 by the general procedure gave 14 in 82% yield: mp 183° C. (aq. EtOH): UV λ$_{max}$ nm (ε×10$^{-3}$): (pH 1) 299 (13.9), 310 (16.2), 324 (11.5): (pH 7) 210 (10.5), 283 (11.6), 297 (sh) (10.3), 310 (10.1), 326 (sh) (7.2): (pH 11) 283 (11.4), 297 (sh) (10.3), 309 (10.0), 326 (sh) (7.2): $^1$H NMR (Me$_2$SO-d$_6$) δ3.44 (m, 2, C$_5'$CH$_2$), 3.78 (m, 1, C$_4'$H), 4.02 and 4.15 (2 m, 2, C$_2'_3'$H), 4.11 (s, 3, OCH$_3$), 5.83 (q, 1, C$_1'$H, collapsed to a d, J=5.6 Hz, after deuteration), 8.59 and 8.82 (2 s, 2, C$_2$H and C$_6$H) and 8.71 (d, 1, J=10.0 Hz, NH). Anal. (C$_{12}$H$_{15}$N$_5$O$_5$.1.5H$_2$O) C, H, N.

EXAMPLE 14

4-Methoxy-8-(α-D-ribofuranosylamino)pyrimido[5,4-d]pyrimidine (17)

Compd 4 was transformed to 16 via the intermediate 15 in a similar way as described above for 13. The overall yield of 16 was 65%: mp 105° C. (EtOH): $^1$H NMR (Me$_2$SO-d$_6$) δ1.37 and 1.56 (2 s, 6, 2CH$_3$), 3.54 (m, 2, C$_5'$CH$_2$), 4.02 (m, 1, C$_4'$H), 4.12 (s, 3, OCH$_3$), 4.85 (m, 2, C$_2'_3'$H), 5.09 (t, 1, C$_5'$OH), 6.16 (q, 1, C$_1'$H, collapsed to a d after deuteration, J=4.6 Hz), 7.83 (d, 1, J=10.4 Hz, NH), 8.67 and 8.86 (2 s, 2, C$_2$H and C$_6$H). Anal. (C$_{15}$H$_{19}$N$_5$O$_5$) C, H, N.

Deisopropylidenation of 16 with aqueous TFA by the general procedure furnished 71% yield of 17: mp 213° C. (H$_2$O): $^1$H NMR (Me$_2$SO-d$_6$) δ3.44 (m, 2, C$_5'$CH$_2$), 3.84, 3.99 and 4.18 (3 m, 3, C$_4'_2'_3'$H), 4.11 (s, 3, OCH$_3$), 6.00 (q, 1, C$_1'$H, collapsed to a d after deuteration, J=5.5 Hz), 8.39 (d, 1, J=10.3 Hz, NH), 8.60 and 8.83 (2 s, 2, C$_2$H and C$_6$H). Anal. (C$_{12}$H$_{15}$N$_5$O$_5$) C, H, N.

EXAMPLE 15

2,6-Dichloro-4-benzyloxy-8-(2,3-O-isopropylidene-β-D-ribofuranosylamino)pyrimido[5,4-d]pyrimidine (18)

To a stirred solution of 3 (0.84 g, 2 mmol) in dry BnOH (3 mL) was added Et$_3$N (0.41 mL, 3 mmol) and the mixture was stirred at ambient temperature for 24 h with the exclusion of moisture. The dark colored reaction mixture was washed with water (2×20 mL) and hexanes (3×20 mL) to furnish a gummy residue, which on purification by flash column chromatography using hexanes/EtOAc (7:3, v/v) as the eluent afforded 0.84 g (85%) of 18: mp 178° C. (EtOH): $^1$H NMR (CDCl$_3$) δ1.36 and 1.59 (2 s, 6, 2CH$_3$), 2.65 (br s, 1, C$_5'$OH), 3.91 (m, 2, C$_5'$CH$_2$), 4.43 (m, 1, C$_4'$H), 4.80 and 4.99 (2 m, 2, C$_2'_3'$H), 5.66 (s, 2, CH$_2$Ph), 6.22 (d of d, 1, C$_1'$H, collapsed to a br s after deuteration), 7.33–7.55 (m, 5, CH$_2$Ph) and 8.68 (d, 1, J=10.4 Hz, NH). Anal. (C$_{21}$H$_{21}$Cl$_2$N$_5$O$_5$) C, H, N, Cl.

EXAMPLE 16

2-6-Dichloro-8-(2,3-O-isopropylidene-β-D-ribofuranosylamino)pyrimido[5,4-d]pyrimidin-4(3H)-one (19)

A mixture of 18 (2.47 g, 5 mmol) and Pd/C (10%, 1 g) in dry dioxane (100 mL) was hydrogenated at atmospheric pressure for 4 h. The catalyst was removed by filtration and the filtrate was evaporated to dryness. The residue was purified by flash chromatography to furnish 1.0 g (50%) of 19: mp 248° C. (d): $^1$H NMR (Me$_2$SO-d$_6$) δ1.27 and 1.46 (2 s, 6, 2CH$_3$), 3.51 (m, 2, C$_5'$CH$_2$), 4.14 (m, 1, C$_4'$H), 4.79 (m, 2, C$_2'_3'$H), 5.44 (t, 1, C$_5'$OH), 5.90 (d of d, 1, C$_1'$H, collapsed to a d on deuteration, J=1.4 Hz) and 8.56 (d, 1, J=10.6 Hz, NH). Anal. (C$_{14}$H$_{15}$Cl$_2$N$_5$O$_5$) C, H, N, Cl.

EXAMPLE 17

8-(β-D-Ribofuranosylamino)pyrimido[5,4-d]pyrimidin-4(3H)-one (21)

Compd 19 on deisopropylidenation with aqueous TFA by the general procedure gave 71% yield of 2,6-dichloro-8-(β-D-ribofuranosylamino)pyrimido[5,4-d]pyrimidin-4(3H)-one: mp 200° C. (d): UV λ$_{max}$ nm (ε×10$^{-3}$): (pH 1) 229 (8.4), 286 (17.9), 324 (7.3), 339 (6.9): (pH 7) 291 (18.3), 323 (11.2), 338 (8.3): (pH 11) 291 (18.2), 323 (11.2), 338 (8.3): $^1$H NMR (Me$_2$SO-d$_6$) δ3.84 (m, 1, C$_4'$H), 3.96 and 4.14 (2 t, 2, C$_2'_3'$H), 5.82 (q, 1, C$_1'$H, collapsed to a d of J=5.6 Hz after deuteration), and 8.10 (d, 1, J=10.0 Hz, NH). Anal. Calcd for C$_{11}$H$_{11}$Cl$_2$N$_5$O$_5$.0.5H$_2$O: C, 35.40: H, 3.24: N, 18.76. Found: C, 35.27: H, 3.03: N, 18.38.

Catalytic hydrogenation of the above dichloro compound by the general procedure gave the title compd in a 66% yield: mp 220° C. (d): UV λ$_{max}$ (ε×10$^{-3}$) (pH 1) 294 (18.2), 309 (16.5), 323 (8.9): (pH 7) 280 (14.1), 315 (7.9), 328 (5.7): (pH 11) 287 (14.6), 313 (10.5), 328 (7.3): $^1$H NMR (Me$_2$SO-d$_6$) δ3.80 (m, 1, C$_4'$H), 3.96 and 4.11 (2 m, 2, C$_2'_3'$H), 4.77 (t, 1, C$_5'$OH), 5.31 and 5.64 (2 m, 2, C$_2'_3'$OH), 5.95 (q, 1, C$_1'$H, collapsed to a d after deuteration, J=5.4 Hz), 8.05 (d, 1, J=10.0 Hz, NH), 8.18 and 8.49 (2 s, 2, C$_2$H and C$_6$H) and 12.5 (br s, 1, NH). Anal. (C$_{11}$H$_{13}$N$_5$O$_5$.0.5H$_2$O) C, H, N.

EXAMPLE 18

2,6-Dichloro-4-methylamino-8-(2,3-O-isopropylidene-β-D-ribofuranosylamino)pyrimido[5,4-d]pyrimidine (22)

To a solution of 3 (0.84 g, 2 mmol) in dry CH$_3$CN (80 mL) was added an ethanolic solution of CH$_3$NH$_2$ (0.52 mL, 5 mmol, 30%) at 0° C. and the mixture was stirred for 1 h. The solvent was evaporated and the residue was purified by crystallization from EtOH/hexanes to furnish 0.66 g (79%) of 22: mp 192° C.: $^1$H NMR (Me$_2$SO-d$_6$) δ1.28 and 1.46 (2 s, 6, 2CH$_3$), 2.92 (d, 3, J=5.3 Hz, NHCH$_3$, collapsed to a s after deuteration), 3.54 (m, 2, C$_5'$CH$_2$), 4.19 (m, C$_4'$H), 4.83 (m, 2, C$_2'_3'$H), 5.61 (t, 1, C$_5'$OH), 5.95 (d, 1, J=6.3 Hz, collapsed to a br s after deuteration), 8.82 (d, 1, J=5.3 Hz, NHCH$_3$) and 9.13 (d, 1, J=6.3 Hz, NH). Anal. (C$_{15}$H$_{18}$Cl$_2$N$_6$O$_4$) C, H, N, Cl.

EXAMPLE 19

4-Methylamino-8-(2,3-O-isopropylidene-β-D-ribofuranosylamino)pyrimido[5,4-d]pyrimidine (23)

Catalytic hydrogenation of 22 by the general procedure gave the title compd in 65% yield: mp 130° C.

(EtOH): $^1$H NMR (Me$_2$SO-d$_6$) δ1.28 and 1.46 (2 s, 6, 2CH$_3$), 2.96 (d, 3, J=5.40 Hz, NHCH$_3$, collapsed to a s after deuteration), 3.54 (m, 2, C$_5'$CH$_2$), 4.18 (br s, 1, C$_4'$H), 4.80 (m, 2, C$_2'{}_3'$H), 5.56 (t, 1, C$_5'$OH), 6.10 (d, 1, J=10.5 Hz, C$_1'$H, collapsed to a br s after deuteration), 8.39 (d, 1, J=5.4 Hz, NHCH$_3$), 8.43 and 8.50 (2 s, 2, C$_2$H and C$_6$H), and 8.83 (d, 1, J=10.5 Hz, NH). Anal. (C$_{15}$H$_{20}$N$_6$O$_4$) C, H, N.

EXAMPLE 20

4-Methylamino-8-(β-D-ribofuranosylamino)-pyrimido[5,4-d]pyrimidine (24)

Deisopropylidenation of 23 following the general procedure gave 24 in 60% yield: mp 230° C. (EtOH): UV λ$_{max}$ (ε×10$^{-3}$) (pH 1) 292 (11.3), 306 (sh) (10.3), 322 (10.0), 336 (7.4): (pH 7) 297 (11.5), 303 (sh) (11.4), 318 (11.2), 334 (7.7): (pH 11) 296 (12.0), 302 (12.0), 317 (11.8), 335 (7.9): $^1$H NMR (Me$_2$SO-d$_6$) δ2.98 and 3.00 (2 s, 3, NHCH$_3$), 5.72 and 6.0 (2 dd, 1, C$_1'$H), 8.21 and 8.95 (d, 1, J=10.0 Hz, NH), 8.47 and 8.51 (2 s, 2, C$_2$H and C$_6$H) and other sugar protons. Anal. (C$_{12}$H$_{16}$N$_6$O$_4$.0.5-H$_2$O) C, H, N.

EXAMPLE 21

2,6-Dichloro-4-dimethylamino-8-(2,3-O-isopropylidene-β-D-ribofuranosylamino)pyrimido[5,4-d]pyrimidine (25)

To a stirred solution of 3 (0.42 g, 1 mmol) in dry CH$_3$CN (25 mL), cold HN(CH$_3$)$_2$ (0.20 mL, 3 mmol) was added at 0° C. TLC (EtOAc:hexanes, 3:7) indicated formation of a high Rf compound (in 5 min). The reaction mixture was evaporated to dryness, the residue was adsorbed on silica gel and purified by flash column chromatography to furnish 0.36 g (84%) of 25: mp 208° C. (EtOH): $^1$H NMR (CDCl$_3$) δ1.39 and 1.61 (2 s, 6, 2CH$_3$), 2.82 (t, 1, C$_5'$OH), 3.18 [s, 6, N(CH$_3$)$_2$], 3.85 (m, 2, C$_5'$CH$_2$), 4.32 (m, 1, C$_4'$H), 4.82 and 4.97 (2 m, 2, C$_2'{}_3'$H), 6.20 (dd, 1, C$_1'$H), 7.73 (d, 1, J=10.8 Hz, NH). Anal. (C$_{16}$H$_{20}$Cl$_2$N$_6$O$_4$) C, H, N, Cl.

EXAMPLE 22

4-Dimethylamino-8-(2,3-O-isopropylidene-β-D-ribofuranosylamino)pyrimido[5,4-d]pyrimidine (26)

Catalytic hydrogenation of 25 by the general procedure furnished 26 in 70% yield: mp 180° C. (EtOH): $^1$H NMR (Me$_2$SO-d$_6$) δ1.28 and 1.46 (2 s, 6, 2CH$_3$), 3.40-3.60 [br s, 6, N(CH$_3$)$_2$], 3.53 (m, 2, C$_5'$CH$_2$), 4.18 (m, 1, C$_4'$H), 4.76 and 4.82 (2 m, 2, C$_2'{}_3'$H), 5.54 (t, 1, C$_5'$OH), 6.10, (q, 1, J=10.6 Hz, C$_1'$H, collapsed to a d on deuteration, J=1.7 Hz), 8.43 and 8.46 (2 s, 2, C$_2$H and C$_6$H), 8.82 (d, 1, J=10.6 Hz, NH). Anal. (C$_{16}$H$_{22}$N$_6$O$_4$.0.5H$_2$O) C, H, N.

EXAMPLE 23

4-Dimethylamino-8-(β-D-ribofuranosylamino)-pyrimido[5,4-d]pyrimidine (27)

Deisopropylidenation of 26 by the general procedure furnished 27 in 75% yield: mp 231° C. (EtOH): UV λ$_{max}$ nm (ε×10$^{-3}$): (pH 1) 300 (16.4), 320 (15.0), 336 (17.0), 351 (12.8): (pH 7) 210 (19.9), 307 (19.6), 320 (18.5), 334 (17.5), 351 (12.8): (pH 11) 306 (18.8), 320 (17.9), 334 (17.0), 351 (12.5): $^1$H NMR (Me$_2$SO-d$_6$) δ3.31-4.13 [m, 11, N(CH$_3$)$_2$, C$_5'$CH$_2$, C$_2'{}_3'{}_4'$H], 5.58 and 5.97 (2 q, 1, C$_1'$H, collapsed to 2 d after deuteration, J=5.3 Hz) 8.29 and 8.97 (d, 1, J=10.5 Hz, NH), 8.46 and 8.47 (2 s, 2, C$_2$H and C$_6$H). Anal. (C$_{13}$H$_{18}$N$_6$O$_4$) C, H, N.

EXAMPLE 24

2-Chloro-4,6-diamino-8-(2,3-O-isopropylidene-D-ribofuranosylamino)pyrimido[5,4-d]pyrimidine (33)

A mixture of 6 (1.41 g, 3.5 mmol) and liquid NH$_3$ (50 mL) was stirred in a sealed reaction vessel at room temperature for 6 days. After removal of NH$_3$, the residue was purified by flash chromatography using EtOAc:hexanes (3:7) as eluent to give two nucleoside products in the order described: (i) compd 33, crystallized from EtOH to give 0.81 g (59%): mp 291° C.: $^1$H NMR (Me$_2$SO-d$_6$) δ1.27 and 1.45 (2 s, 6, 2CH$_3$), 3.53 (m, 2, C$_5'$CH$_2$), 4.11 (m, 1, C$_4'$H), 4.79 (m, 2, C$_2'{}_3'$H), 5.44 (t, 1, C$_5'$OH), 6.04 (d, 1, J=10.8 Hz, C$_1'$H), 6.45 (br s, 2, NH$_2$), 7.21 and 8.13 (2 br s, 2, NH$_2$), 8.40 (d, 1, J=10.80 Hz, NH). Anal. (C$_{14}$H$_{18}$ClN$_7$O$_4$.0.5H$_2$O) C, H, N, Cl.

(ii) The α-anomer of 33: 0.20 g (15% yield as foam): $^1$H NMR (Me$_2$SO-d$_6$) δ1.28 and 1.46 (2 s, 6, 2CH$_3$), 3.61 (m, 2, C$_5'$CH$_2$), 4.21 (br s, 1, C$_4'$H), 4.70 and 4.84 (d, 2, C$_2'{}_3'$H), 5.55 (t, 1, C$_5'$OH), 5.89 (d, 1, J=10.7 Hz, C$_1'$H), 6.19 (br s, 2, NH$_2$), 7.28 and 7.47 (2 br s, 2, NH$_2$) and 8.78 (d, 1, J=10.7 Hz, NH). Anal. Calcd for C$_{14}$H$_{18}$ClN$_7$O$_4$: C, 43.81: H, 4.72: N, 25.54: Cl, 9.23. Found: C, 43.87: H, 4.75: N, 25.65: Cl, 9.09.

EXAMPLE 25

4,6-Diamino-8-(2,3-O-isopropylidene-β-D-ribofuranosylamino)pyrimido[5,4-d]pyrimidine (34)

Catalytic hydrogenation of 33 by the general procedure furnished 34 in 72% yield: mp 150° C. (foam): $^1$H NMR (Me$_2$SO-d$_6$) δ1.27 and 1.45 (2 s, 6, 2CH$_3$), 3.61 (m, 2, C$_5'$CH$_2$), 4.13 (br s, 1, C$_4'$H), 4.80 (m, 2, C$_2'{}_3'$H), 5.47 (t, 1, C$_5'$OH), 6.05 (dd, 1, C$_1'$H, collapsed to a s on deuteration), 6.37 (br s, 2, NH$_2$), 6.71 and 7.50 (2 br s, 2, NH$_2$), 8.05 (s, 1, C$_2$H) and 8.54 (d, 1, J=10.5 Hz, NH). Anal. (C$_{14}$H$_{19}$N$_7$O$_4$.0.25H$_2$O) C, H, N.

EXAMPLE 26

4,6-Diamino-8-(β-D-ribofuranosylamino)pyrimido[5,4-d]pyrimidine (35)

Deisopropylidenation of 34 by the general procedure gave the title compd, which was isolated as its TFA salt in 66% yield: mp 170° C. (d): UV λ$_{max}$ nm (ε×10$^{-3}$): (pH 1) 244 (13.7), 269 (15.3), 334 (7.1), 350 (6.6): (pH 7) 242 (124), 280 (14.6), 343 (8.0): (pH 11) 210 (21.1), 242 (12.4), 281 (14.4), 344 (8.0): $^1$H NMR (Me$_2$SO-d$_6$) δ3.20-4.21 (m, 5, C$_2'{}_3'{}_4'$H and C$_5'$H$_2$), 5.90-5.98 (q, 1, C$_1'$H, collapsed to a d on deuteration, J=5.61 Hz) 7.81 (br s, 4, 2NH$_2$), 8.30 (s, 1, C$_2$H), 8.73 and 9.20 (2 br s, 1, NH). Anal. (C$_{11}$H$_{15}$N$_7$O$_4$.TFA) C, H, N.

EXAMPLE 27

4-Amino-6-chloro-8-(2,3-O-isopropylidene-β-D-ribofuranosylamino)pyrimido[5,4-d]pyrimidine (36)

Controlled hydrogenation of 6 at atmospheric pressure for 16 h gave 36 in 65% yield following the general work-up procedure: mp 206° C. (EtOH): $^1$H NMR (Me$_2$SO-d$_6$) δ1.28 and 1.47 (2 s, 6, 2CH$_3$), 3.57 (m, 2, C$_5'$CH$_2$), 4.21 (br s, 1, C$_4'$H), 4.82 (m, 2, C$_2'{}_3'$H), 5.64 (br s, 1, C$_5'$OH), 5.97 (d, 1, J=10.0 Hz, C$_1'$H), 7.79 and 8.06 (2 br s, 2, NH$_2$), 8.35 (s, 1, C$_2$H) and 9.24 (d, 1, J=10.0 Hz, NH). Anal. (C$_{14}$H$_{17}$ClN$_6$O$_4$) C, H, N, Cl.

EXAMPLE 28

4-Amino-6-chloro-8-(β-D-ribofuranosylamino)-pyrimido[5,4-d]pyrimidine (37)

Deisopropylidenation of 36 by the general procedure gave 6-chloro-ARPP in 67% yield: mp 205° C. (d): UV $\lambda_{max}$ nm ($\epsilon \times 10^{-3}$): (pH 1) 290 (16.8), 328 (12.2), 342 (9.5): (pH 7) 291 (16.5), 308 (sh) (13.0), 322 (13.0), 337 (9.7): (pH 11) 291 (16.4), 308 (sh) (13.0), 323 (12.9), 337 (9.7): $^1$H NMR (Me$_2$SO-d$_6$) δ3.41–4.12 (m, 5, C$_2'_3'_4'$H and C$_5'$CH$_2$), 5.70 and 5.86 (2 q, 1, C$_1'$H, collapsed to 2d on deuteration, J=6.0 Hz), 7.79 and 8.07 (2 br s, 2, NH$_2$), 8.38 (s, 1, C$_2$H), 8.45 and 8.90 (2 d, 1, J=10.9 Hz, NH). Anal. (C$_{11}$H$_{13}$ClN$_6$O$_4$.0.75H$_2$O) C, H, N.

EXAMPLE 29

4,6-Dichloro-8-(2,3-O-isopropylidene-D-ribofuranosylamino)pyrimido[5,4-d]pyrimidine (29)

Condensation of dry 4,6,8-trichloropyrimido[5,4-d]pyrimidine (28, 3.52 g, 15 mmol) with 2 (3.61 g, 10 mmol) was carried out in a similar way as described for the preparation of 3, and a 3:7 mixture of α- and β-anomers of 29 was obtained as a foam in 45% yield. Attempted crystallization and extended solvent contact decomposed 29 into unidentified compounds: UV (MeOH) $\lambda_{max}$ nm ($\epsilon \times 10^{-3}$): 244 (5.8), 287 (8.0), 310 (sh) (8.3), 329 (11.1), 348 (sh) (7:6): $^1$H NMR (CDCl$_3$) δ1.40 and 1.62 (2 s, 6, 2CH$_3$, β), 1.48 and 1.72 (2 s, 6, 2CH$_3$, α), 2.71 (br s, 1, C$_5'$OH, β), 2.78 (t, 1, C$_5'$OH, α), 6.25 (dd, 1, C$_1'$H, α), 6.36 (d, 1, C$_1'$H, β), 8.40 (d, 1, J=10.6 Hz, NH, α), 8.93 (s, 1, C$_2$H, β), 9.03 (s, 1, C$_2$H, α), 9.08 (d, 1, J=10.5 Hz, NH, β) and other sugar protons. Anal. (C$_{14}$H$_{15}$Cl$_2$N$_5$O$_5$.0.5n-BuOH) C, H, N, Cl.

EXAMPLE 30

4-Benzyloxy-6-chloro-8-(2,3-O-isopropylidene-β-D-ribofuranosylamino)pyrimido[5,4-d]pyrimidine (30)

The title compd was prepared from 29 in 65% yield, following the procedure as described for the preparation of 18. Pure β-anomer, being the less soluble compound crystallized from EtOH and was found to be quite stable in solution compared to its precursor 29: mp 188°–190° C.: $^1$H NMR (CDCl$_3$) δ1.33 and 1.55 (2 s, 6, 2CH$_3$), 2.68 (t, 1, C$_5'$OH), 3.88 (m, 2, C$_5'$CH$_2$), 4.40 (br s, 1, C$_4'$H), 4.76 and 4.96 (2 m, 2, C$_2'_3'$H), 5.63 (s, 2, CH$_2$Ph), 6.22 (dd, 1, C$_1'$H), 7.31–7.52 (m, 5, CH$_2$Ph) and 8.64 (d, 1, J=10.0 Hz, NH). Anal. (C$_{21}$H$_{22}$ClN$_5$O$_5$) C, H, N, Cl.

EXAMPLE 31

6-Chloro-8-(2,3-O-isopropylidene-β-D-ribofuranosylamino)pyrimido[5,4-d]pyrimidin-4-(3H)-one (31)

Following the procedure as described for the preparation of 19, compd 30 was hydrogenated to give 31 in 69% yield: mp >220° C. (d): $^1$H NMR (Me$_2$SO-d$_6$) δ1.25 and 1.43 (2s, 6, 2 CH$_3$), 3.50 (m, 2, C$_5'$CH$_2$), 4.19 (m, 1, C$_4'$H), 4.71–4.80 (m, 2, C$_2'_3'$H), 5.94 (d, 1, J=10.0 Hz, C$_1'$H), 8.14 (s, 1, C$_2$H), 9.07 (d, 1, J=10.0 Hz, NH), and 12.9 (br s, 1, N$_3$H). Anal. (C$_{14}$H$_{16}$ClN$_5$O$_5$.H$_2$O) C, H, N.

EXAMPLE 32

6-Chloro-8-(β-D-ribofuranosylamino)pyrimido[5,4-d]pyrimidin-4(3H)-one (32)

Deisopropylidenation of 31 by aqueous TFA following the general procedure furnished the title compd in 58% yield: mp 180°–182° C. (d): UV $\lambda_{max}$ nm ($\epsilon \times 10^{-3}$): (pH 1) 230 (6.1), 277 (sh) (15.3), 285 (16.2), 310 (sh) (8.8), 320 (9.4), 334 (7.0): (pH 7) 228 (6.1), 277 (sh) (15.3), 285 (15.8), 308 (sh) (8.8), 320 (9.4), 334 (6.9): (pH 11) 290 (15.3), 308 (sh) (12.9), 319 (10.8), 334 (7.8): $^1$H NMR (Me$_2$SO-d$_6$) δ3.48 (m, 2, C$_5'$CH$_2$), 3.83 (m, 1, C$_4'$H), 3.98–4.06 (m, 2, C$_2'_3'$H), 5.54 and 5.84 (2 q, 1, collapsed to 2d on deuteration, J=5.5 Hz, C$_1'$H), 8.20 (s, 1, C$_2$H), 8.30 and 9.0 (2 d, 1, J=10.0 Hz, NH), 12.95 (br s, 1, N$_3$H) and other sugar protons. Anal. (C$_{11}$H$_{12}$ClN$_5$O$_5$.0.25EtOH) C, H, N, Cl.

EXAMPLE 33

Antiviral activity

Cell culture antiviral studies against Herpes 2, parainfluenza 3 and Vaccinia indicate antiviral activity for compounds 11, 14 and 17 as tested in parallel with ARPP (8). These results are summarized in Table 1.

TABLE 1

| | In Vitro Antiviral and Antitumor Activity | | | | | |
|---|---|---|---|---|---|---|
| | Antiviral (VR)$^a$ | | | Antitumor (ID$_{50}$)$^b$ | | |
| Compd | HSV2$^c$ | VV$^d$ | PI3$^e$ | L1210 | WI-L2 | LoVo/L |
| 8 | 0.8 | 1.3 | 0.7 | 0.8 | 0.2 | 7.0 |
| 14 | 0.2 | 1.0 | 0.7 | 0.04 | 0.06 | 0.28 |
| 11 | 0.2 | 1.0 | 1.4 | 0.38 | 0.25 | 1.0 |
| 17 | 0.1 | 0.9 | 0.7 | 2.9 | 2.5 | 18.7 |

$^a$(VR) virus ratings by convention >1.0 indicate marked antiviral activity; 0.5 to 0.9 indicate moderate activity, and <0.5 indicate weak or no activity;
$^b$(ID$_{50}$) inhibitory dose is the μM concentration of the compound that inhibits tumor cell growth by 50% as compared to the untreated controls;
$^c$herpes simplex virus type 2 (MS strain) cell line in Vero cells;
$^d$vaccinia virus (Elstree strain) cell line in HeLa cells;
$^e$parainfluenza 3 (C243 strain) cell line in Vero cells.

EXAMPLE 34

Human Immunodeficiency Virus

Compound 8 was evaluated by the National Cancer Institute for in vitro activity against human immunodeficiency virus (HIV: cell line:CEM-V). In this test the compound was screened using human "host" cells with and without virus. The test is conducted for seven days (during which time infected, non-drug treated control cells are largely or totally destroyed by the virus), and then the number of remaining viable cells are determined. Two parameters are extracted from the test: the EC$_{50}$ (or EC$_{90}$), representing the concentration of drug that resulted in a 50% reduction of the viral cytopathic effect and the IC$_{50}$ (or IC$_{90}$), representing the concentration of drug resulting in 50% growth inhibition (derived from the normal, unifected cells). A therapeutic index (TI) can be calculated as the IC/EC ratio.

At $9.51 \times 10^{-8}$, compound 8 exhibited a 50% reduction of viral cytopathic effect (EC$_{50}$) and at $7.68 \times 10^{-7}$ compound 8 exhibited a 90% reduction of viral cytopathic effect (EC$_{90}$). The IC$_{50}$ and IC$_{90}$ were $1.95 \times 10^{-6}$ and $6.6 \times 10^{-6}$, respectively, thus the compound exhibited therapeutic indices at 50% and 90% of $2.05 \times 10^1$ and $8.60 \times 10^0$, respectively.

EXAMPLE 35

In Vitro Antitumor Activity

In vitro cytotoxicity analysis was performed by using the following cell lines: L1210 (a murine leukemia), WI-L2 (a human B-lymphoblast), and LoVo/L (a human colon carcinoma). Cells were grown in RPMI 1640 medium supplemented with 10% fetal bovine serum, 20 mM HEPES, pH 7.4, and 2 mM glutamine. The cytotoxicity determinations were carried out in 96-well microtiter dishes containing a starting number of $5-10 \times 10^3$ cells per well and 0.1–100 μM concentrations of the compounds in triplicate wells. L1210 and WI-L2 were incubated with the compounds at 37° C. for 3 days, while Lovo/L was incubated for 5 days. After this time period, 25 μL of 4 mg/mL 3-(4,5-dimethylthiazol-2-yl)-2,5-diphenyltetrazolium bromide was added to each well and incubation was continued for 2 to 5 h. The formazan product was dissolved in isopropanol containing 0.04M HCl and the absorbance was determined with a microtiter plate reader. The absorbance was proportional to the number of cells. The absorbance values were used to calculate the $ID_{50}$ value for each compound, the concentration which inhibited cell growth to 50% of the value for untreated, control cells. The results for compounds 8, 11, 14 and 17 are also summarized in Table 1.

EXAMPLE 36

In Vivo Antitumor Activity

Compounds 8, 11, 14 and 17 were comparatively evaluated in vivo for efficacy against L1210 in $BDF_1$ mice. The results are shown in Table 2.

TABLE 2

| Compound Number | Dosage mg/kg/inj. | Postinoculation Lifespan (% T/C) |
|---|---|---|
| 8 | 173[1] | 162 |
| 11 | 22[1] | 138 |
| 14 | 62[2] (173)[1] | 182 |
| 17 | 37[1] | 116 |

[1]Maximum water-soluble dosage.
[2]Maximum non-lethal dosage. Maximum water-soluble dosage is shown in parentheses.

Mice were inoculated i.p. with $1 \times 10^6$ L1210 cells 24 hr before qd, day 1, i.p. drug delivery. Drugs were solubilized in water and delivered at the rate of 0.01 ml/g mouse weight. Then control mice/drug were injected i.p. with equivalent volumes of a 0.9% solution of NaCl, the means and standard deviations reflecting the post-inoculation life spans of these mice ranged from $6.30 \pm 0.48$ to $6.60 \pm 0.97$ days.

Compound (8) and the α-anomer 11 differ both in their solubility in water and in their efficacy against L1210. Thus, the maximum water solubility of 8 was 17.3 mg/mL as compared to 2.2 mg/mL for 11, and when administered qd, day 1, the former produced a T/C of 162 as opposed to 138 for the latter. Neither drug was lethally toxic at its maximum soluble dosage. In a similar manner, compound (14) and the α-anomer 17 were tested. Compound 17 was soluble in water to a maximum of 3.7 mg/mL and produced a treatment T/C of 116. Conversely, 14 was soluble up to 17.3 mg/mL and was lethally toxic at that level for all treated mice. Compound 14 also caused death for 1/6 treated mice when made up at 10.4 mg/mL. The maximum non-lethal concentration of MRPP was 6.2 mg/mL, and when it was administered at 62 mg/kg produced a T/C of 182. Taken collectively, it appears from these results that the β-anomers have greater solubility than the α-anomers and when administered qd day 1, are more effective in the treatment of L1210 leukemia.

Compounds of the invention were also tested for certain biochemical properties. Compounds of the invention were studied for their effect on de novo purine biosynthesis by observing inhibition of incorporation of [$^{14}$C]formate into the acid-soluble fraction of WI-L2 cells (see Table 3). Compounds (8) and (14) showed the greatest inhibitory activity and were active at concentrations as low as 0.25 μM. However, 8 and 14 (100 μM) were not cytotoxic to WI-L2 cells deficient in adenosine kinase activity. Direct inhibition of WI-L2 adenosine kinase by compound 14 was observed as a decrease in the rate of [$^{14}$C]AMP formation from [$^{14}$C]adenosine. Compound 14 demonstrated a Ki value of 8 μM at an apparent Km value for adenosine of 0.9 μM. This suggests that phosphorylation of 14 by adenosine kinase is required for inhibitory activity.

The formation of intracellular ARPP 5'-monophosphate but no higher phosphate analogues has been shown by SAX-HPLC results, however, two anomeric species were detected within the monophosphate region of the chromatogram. The similar appearance of two species was also seen in aqueous solution for ARPP anlayzed by reverse-phase HPLC. When ARPP was treated with adenosine deaminase as reagent, the preferential disappearance of the β-anomer (60% conversion in 5 min) was followed by a much slower decrease in the area of the α-anomer peak. This would be expected where the rate of anomerization is slow compared to the rate of deamination. The deamination product (21) similarly equilibrated from pure β-anomer into a mixture of α- and β-anomers. Compound 14 was less active as a substrate for adenosine deaminase and less than 10% was deaminated in 18 h under the same conditions as described for ARPP. Prior addition of 1 μM coformycin to the assay completely prevented the deamination of ARPP.

The actual rate of anomerization was investigated in the absence of added protein by incubating a buffered sample of compound 14 at 37° C. After 9 h the solution analyzed by reverse-phase HPLC showed 1.35% of the α-anomer 17 and 0.42% of 21 as an anomeric mixture. Thus, the α-anomer 17 was inactive in the purine de novo assay over the short term (4 h, see Table 3) but demonstrated the inhibitory activity in separate assays which employed longer incubation times. Compounds 8 and 14 appear to require activation to the 5'-monophosphate and inhibit an early step in de novo purine biosynthesis. The compounds of the invention are capable of crossing the cell membrane, and activated to the 5'-phosphate, thus causing the inhibition of the de novo purine biosynthesis.

EXAMPLE 37

Biochemical Studies

A normal lymphoblast phenotype B cell line, WI-L2 was used. The enzyme-deficient cell lines used in vitro are: HPRT-, a hypoxanthine-guanine phosphorbosyl transferase (EC 2.4.2.8)deficient line and AK-, an adenosine kinase (EC 2.7.1.20)deficient line. Cells were cultured in RPMI 1640 medium containing 5% dialyzed fetal bovine serum, 20 mM Na HEPES, pH 7.5 and 2 mM glutamine and maintained in log phase growth between 0.5 and $12 \times 10^5$ cells/mL. The mutant cell lines were periodically reselected by treatment with 6-thioguanine (HPRT-) or tubercidin (AK-).

HPLC Analysis: Sample components were separated with an LKB model 2150 gradient HPLC system at ambient temperature on an Altex Ultrashere-ODS reverse phase column (Beckman) developed with a linear gradient of buffer A (10 mM $KPO_4'$, pH 3.83) to 20% component B (60% aqueous $CH_3CN$) at a combined flow rate of 1.0 mL/min over 15 min. Ultraviolet (UV) absorbance was monitored with an LKB model 2140 diode array detector. Inhibition of de novo purine biosynthesis: WI-L2 or adenosine kinase-deficient cells were preincubated at 37° C. with drug for various time periods prior to labeling with [$^{14}C$]formate. Enzyme Assays: Adenosine kinase inhibition studies were accomplished by the filter binding assay method. Inhibition studies were done at 37° C. with an assay mixture containing 4 mM ATP, 1.5 mM $MgCl_2$, 5 or 10 $\mu M$ [8-$^{14}C$] adenosine (50 mCi/mmol) and 100 mM Trismaleate, pH 5.5. To prevent the enzymatic breakdown of adenosine, erythro-9-(2-hydroxy-3-nonyl)adenine (EHNA) was added to the cell-free WI-L2 lysate to give 5 $\mu M$ final assay concentration. The assay was started by the addition of protein. The amount of enzyme, time of assay and sampling volume were adjusted to give acceptable conversion of [8-$^{14}C$] adenosine to [8-$^{14}C$]AMP. Each DE-81 filter was spotted with a constant sampling volume and immersed in $H_2O$ (4 L) to terminate the reaction. Filters were washed three times with $H_2O$ (4 L) and once with EtOH (100 mL). Dry filters were placed in scintillation vials and radioactivity was counted with 10 mL toluene-based scintillation cocktail.

Adenosine deaminase substract activity was accomplished by incubating each compound (1.0 mM) in potassium phosphate buffer (100 mM, pH 7.5) with 0.25 units/mL of adenosine deaminase. Samples were analyzed directly on reverse-phase HPLC. Enzymatic conversions were distinguished from hydrolysis by treating a parallel sample with EHNA to inhibit the deaminase activity.

TABLE 3

Comparative effect of compounds of the invention on de novo purine biosynthesis.

| compd | conc $\mu M$ | % of control cell | % of control media | pre-incubation time (h) |
|---|---|---|---|---|
| 8 | 2.5 | 29.9 | 54.6 | 8 |
|  | 0.25 | 79.5 | 71.9 | 8 |
| 14 | 25 | 4.3 | a | 4 |
|  | 2.5 | 2.7 | 41.8 | 8 |
|  | 0.25 | 41.9 | 63.0 | 8 |
| 21 | 50 | 98.2 | 105.9 | 8 |
| 27 | 50 | 50.7 | 85.8 | 8 |
| 37 | 50 | 16.4 | 43.4 | 8 |
| 35 | 50 | 91.2 | 89.8 | 8 |
| 17 | 25 | 98.2 | a | 4 |

$^a$not determined.

De novo purine biosynthesis was measured by the incorporation of $^{14}C$-formate into cellular purine nucleotides or excreted purines after pre-incubation with compound.

TABLE 4

Comparative effect of compounds on $^{14}C$-bicarbonate incorporation into acid soluble pyrimidine (PyrTP, CTP + UTP) and purine (PurTP, ATP + GTP) nucleoside triphosphates.

| compd | conc. ($\mu M$) | PyrTP | PurTP | CAA$^b$ | PydTP | PurTP |
|---|---|---|---|---|---|---|
| 8 | 1.5 | 0 | 0 | 1608 | 0 | 0 |
| 14 | 5.0 | 0 | 0 | 1322 | 0 | 0 |
| 21 | 50.0 | 15691 | 54484 | 0 | 72.3 | 91.5 |
| 27 | 50.0 | 10177 | 40581 | 0 | 46.9 | 68.2 |
| 37 | 15.0 | 13454 | 39833 | 0 | 62.0 | 66.9 |
| 35 | 50.0 | 15267 | 58130 | 0 | 70.4 | 97.7 |
| control | — | 21692 | 59520 | 0 | 100 | 100 | cpm/$10^6$ cells % control$^a$ $^a$Control values expressed in cpm/$10^6$, cells are PydTP [CTP (1415) – UTP (20277)]; PurTP [ATP (52412) + GTP (7106)]. Zero values designate undetectable amounts.
$^b$Carbamyl aspartate.

For delivery to a host inflicted with a neoplastic disease compounds of the invention can be formulated in various formulations to prepare pharmaceutical compositions containing compounds of the invention as active ingredients. The following illustrative examples are given for the formulations of such pharmaceutical compositions utilizing compounds of the invention.

In these examples, Pharmaceutical Preparative Example A illustrates the use of compounds of the invention as injectables suitable for intravenous or other types of injection into the host animal. Pharmaceutical Preparative Example B is directed to an oral syrup preparation, Pharmaceutical Example C to an oral capsule preparation and Pharmaceutical Preparative Example D to oral tablets. Pharmaceutical Preparative Example E is directed to use of compounds of the invention in suitable suppositories. For Pharmaceutical Preparative Examples A through E the ingredients are listed followed by methods of preparing the composition.

EXAMPLE A
INJECTABLES

| Compounds of the Invention | 250 mg-1000 mg |
|---|---|
| Water for Injection USP q.s. | |

The compounds of the invention are dissolved in the water and passed through a 0.22 micron filter. The filtered solution is added to ampoules or vials, sealed and sterilized.

EXAMPLE B
SYRUP
250 mg Active ingredient/5 ml syrup

| Compounds of the Invention | 50.0 g |
|---|---|
| Purified Water USP q.s. or | 200 ml |
| Cherry Syrup q.s. ad | 1000 ml |

The compounds of the invention are dissolved in the water and to this solution the syrup is added with mild stirring.

EXAMPLE C
CAPSULES
100 mg 250 mg or 500 mg

| Compounds of the Invention | 500 g |
|---|---|
| Lactose USP, Anhydrous q.s. or | 200 g |
| Sterotex Powder HM | 5 g |

Combine the compounds of the invention and the Lactose in a twin-shell blender equipped with an intensifier bar. Tumble blend for two minutes, followed by blending for one minute with the intensifier bar and then tumble blend again for one minute. A portion of the blend is then mixed with the Sterotex Powder, passed through a #30 screen and added back to the remainder of the blend. The mixed ingredients are then blended for one minute, blended with the intensifier bar for thirty seconds and tumble blended for an additional minute. Appropriate sized capsules are filled with 141 mg, 352.5 mg or 705 mg of the blend, respectively, for the 100 mg, 260 mg and 500 mg containing capsules.

| EXAMPLE D TABLETS | |
|---|---|
| Compounds of the Invention | 500 g |
| Corn Starch NF | 200.0 g |
| Cellulose Microcrystalline | 46.0 g |
| Sterotex Powder HM | 4.0 g |
| Purified Water q.s. | 300.0 g |

Combine the corn starch, the cellulose and the compounds of the invention together in a planetary mixer and mix for two minutes. Add the water to this combination and mix for one minute. The resulting mix is spread on trays and dried in a hot air oven at 50° C. until a moisture level of 1 and 2 percent is obtained. The dried mix is then milled with a Fitzmill through a #RH2B screen at medium speed. The Sterotex Powder is added to a portion of the mix and passed through a #30 screen and added back to the milled mixture and the total blended for five minutes by drum rolling. Compressed tablets of 150 mg, 375 mg and 750 mg respectively, of the total mix are formed with appropriate sized punches for the 100 mg, 250 mg or 500 mg containing tablets.

| EXAMPLE E SUPPOSITORIES 250 mg, 500 mg or 1000 mg per 3 g | | | |
|---|---|---|---|
| Compounds of the invention | 250 mg | 500 mg | 1000 mg |
| Polyethylene Glycol 1540 | 1925 mg | 1750 mg | 1400 mg |
| Polyethylene Glycol 8000 | 825 mg | 750 mg | 600 mg |

Melt the Polyethylene Glycol 1540 and the Polyethylene Glycol 8000 together at 60° C. and dissolve the compounds of the invention into the melt. Mold this total at 25° C. into appropriate suppositories.

Scheme I

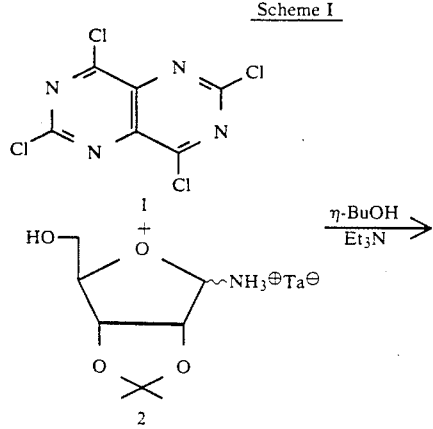

Scheme I
-continued

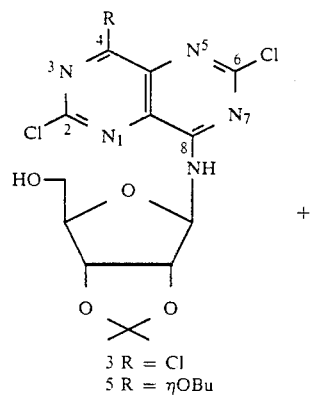

3 R = Cl
5 R = ηOBu

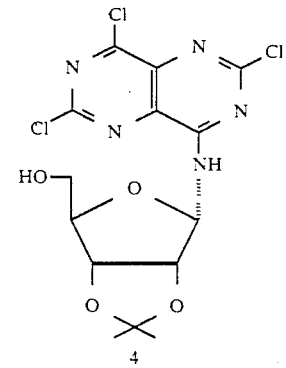

Scheme II

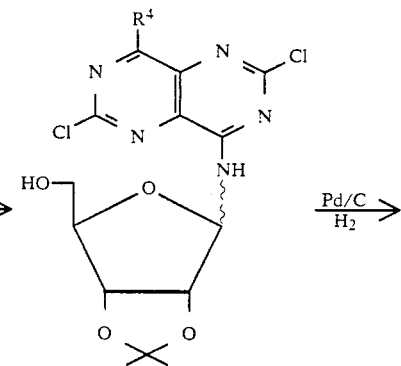

3 or 4 ⟶ Pd/C / H₂ ⟶

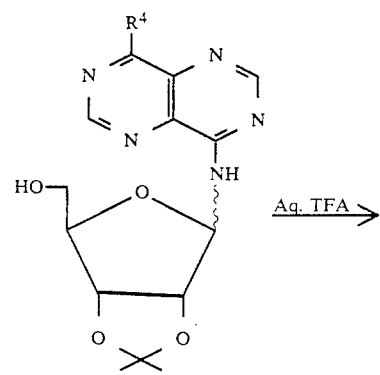

⟶ Aq. TFA ⟶

Scheme II-continued

| | | | | | | | | | |
|---|---|---|---|---|---|---|---|---|---|
| 12 | OCH$_3$ | β | 13 | OCH$_3$ | β | 14 | OCH$_3$ | β | |
| 15 | OCH$_3$ | α | 16 | OCH$_3$ | α | 17 | OCH$_3$ | α | |
| 18 | OCH$_2$Ph | β | | | | | | | |
| 19 | OH* | β | 20 | OH* | β | 21 | OH* | β | |
| 22 | NHMe | β | 23 | NHMe | β | 24 | NHMe | β | |
| 25 | NMe$_2$ | β | 26 | NMe$_2$ | β | 27 | NMe$_2$ | β | | a.c. anomeric configuration;
*Present as the oxo tautomer.

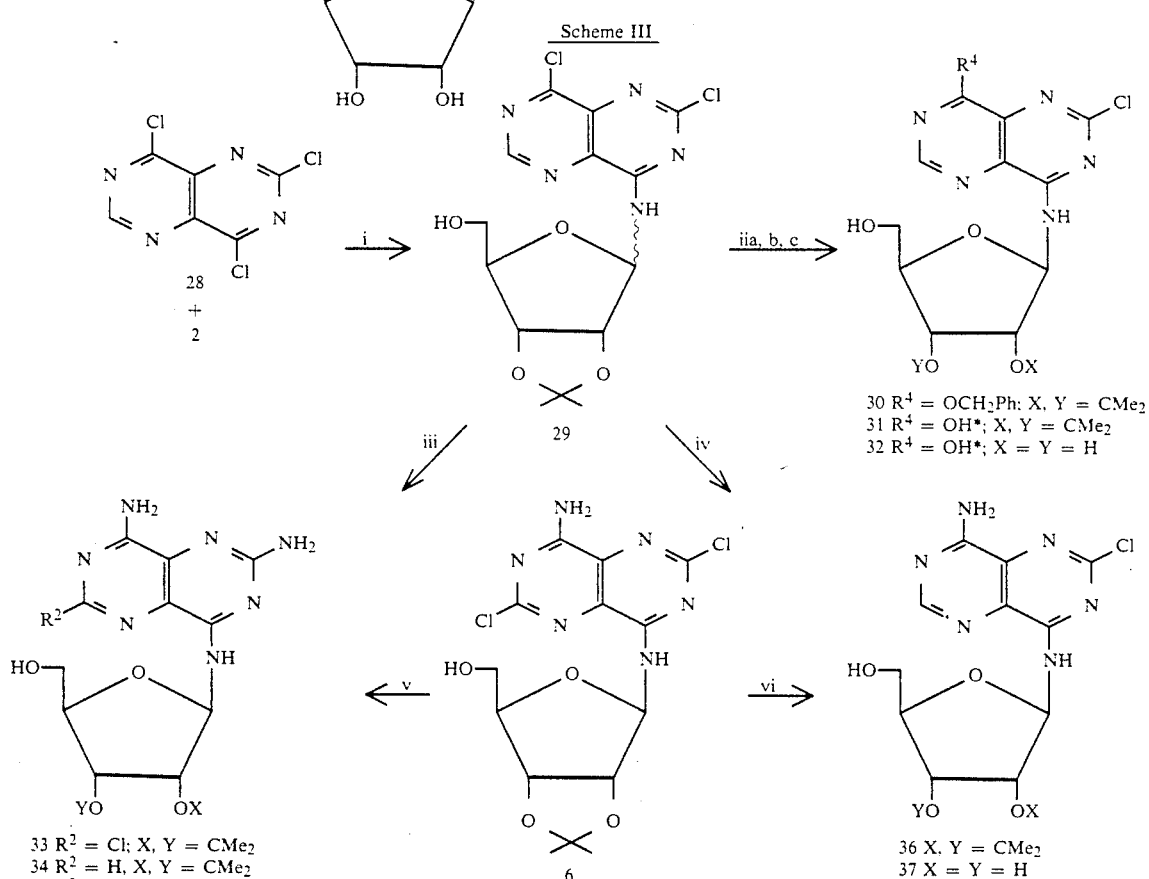

30 R$^4$ = OCH$_2$Ph; X, Y = CMe$_2$
31 R$^4$ = OH*; X, Y = CMe$_2$
32 R$^4$ = OH*; X = Y = H

33 R$^2$ = Cl; X, Y = CMe$_2$
34 R$^2$ = H; X, Y = CMe$_2$
35 R$^2$ = X = Y = H

36 X, Y = CMe$_2$
37 X = Y = H i. n-BuOH, Et$_3$N, RT, oh; iia. BnOH, Et$_3$N, RT; iib. Pd/C, H$_2$, Atmos press; iic. Aq. TFA;
iii. Liq. NH$_3$, RT →  iic; iv. MeOH/NH$_3$, 0° C., 15 min →  iic; v. iii →  iib →  iic; vi. iib →  iic;
*Present as the oxo tautomer.

| compd | R$^4$ | a.c. | compd | R$^4$ | a.c. | compd | R$^4$ | a.c. |
|---|---|---|---|---|---|---|---|---|
| 6 | NH$_2$ | β | 7 | NH$_2$ | β | 8 | NH$_2$ | β |
| 9 | NH$_2$ | α | 10 | NH$_2$ | α | 11 | NH$_2$ | α |

We claim:
1. A pharmaceutical composition containing as its active ingredient an effective amount of the compound 4-methoxy-8-(β-D-ribofuranosylamino)pyrimido[5,4-d]pyrimidine and pharmaceutically acceptable salts thereof in a pharmaceutically acceptable carrier.
2. The compound 4-methoxy-8-(β-D-ribofuranosylamino)pyrimido[5,4-d]pyrimidine.
3. The compound 4-methoxy-8-(α-D-ribofuranosylamino)pyrimido[5,4-d]pyrimidine.

* * * * *